United States Patent [19]
Wagner et al.

[11] Patent Number: 5,866,406
[45] Date of Patent: Feb. 2, 1999

[54] OXIDASE-PRODUCING *ASPERGILLUS NIGER*

[75] Inventors: Fred W. Wagner, Walton; John P. Markwell, Lincoln, both of Nebr.

[73] Assignee: The Board of Regents of the University of Nebraska, Lincoln, Nebr.

[21] Appl. No.: 932,393

[22] Filed: Sep. 17, 1997

Related U.S. Application Data

[63] Continuation of Ser. No. 566,487, Dec. 4, 1995, abandoned, which is a continuation of Ser. No. 421,294, Apr. 13, 1995, abandoned, which is a continuation of Ser. No. 8,095, Jan. 22, 1993, abandoned, which is a continuation of Ser. No. 830,483, Feb. 4, 1992, abandoned, which is a continuation of Ser. No. 474,466, Feb. 2, 1990, abandoned.

[51] Int. Cl.$^6$ ....................................................... C12N 1/14
[52] U.S. Cl. ........................ 435/256.1; 435/190; 435/917
[58] Field of Search ................................ 435/256.1, 190, 435/917

[56] References Cited

U.S. PATENT DOCUMENTS 2,765,233  10/1956  Sarett et al. .
2,926,122   2/1960  Goldsmith et al. .
2,940,904   6/1960  Ohlmeyer .

OTHER PUBLICATIONS

Markwell et al., "*Aspergillus niger* Mutants with Increased Glucose Oxidase Production", Appl. Microbiol. Biotech., 1989, 30:166–169.

Fiedurek et al., "Screening and Mutagenesis of Moulds for the Improvement of Glucose Oxidase Production", *Enzyme Microb. Technol.*, vol. 8; 1986; pp. 734–736.

"Organic Acid Production" Chapter 8 of The Filamentous Fungi, vol. 1, Industrial Mycology, edited by John E. Smith and David R. Berry; by L. B. Lockwood, pp. 140–157; 1975.

"Production of Gluconic Acid, Glucose Oxidase, Fructose, and Sorbase", Microbial Technology, edited by Henry J. Peppler, 1967; Chapter 9, pp. 200–221.

"Sodium Gluconate Production" Fermentation with Aspergillus niger, Industrial and Engineering Chemistry, Feb. 1952, vol. 44 No. 2; pp. 435–440.

"Genetic Approaches to the Production of Primary Metabolites", Primary Metabolism and Industrial Fermentations, Gene Manipulations in Fungi; 1985, pp. 359–401.

"Organic Acid Production", by L. B. Lockwood, Chapter 8, pp. 140–157.

Aspergillus Niger Inalt Producator De Glucozoxidaza (I); Irina Zamfirescu; St. cere. biochim., 26, 2, 129–134 (1983).

"Aspergillus niger mutants with increased glucose oxidase production", Applied Microbiol Biotechnol (1989) 30:166–169; John Markwell, et al.

*Primary Examiner*—Jean C. Witz
*Attorney, Agent, or Firm*—Vincent L. Carney

[57] ABSTRACT

To provide increased levels of oxidase, mutants of *Aspergillus niger* that constitutively synthesize glucose oxidase when grown in a medium having less than 0.1M (molar) glucose are obtained. To obtain mutants, a microorganism is cultured with a substrate having a nutrient, an auxiliary carbon source and a pH-sensitive indicator; and cultures in which the pH has changed as indicated by the pH-sensitive indicator are selected for further growth. More specifically, *Aspergillus niger* that has been subjected to mutagens is cultured with an auxiliary carbon source, methyl red and D-glucose at a low concentration below that which will trigger the production of D-glucose oxidase in the microorganism. Portions of the culture indicated by red are separated and increased. One such mutants has accession number NRRL 18927.

1 Claim, No Drawings

OXIDASE-PRODUCING *ASPERGILLUS NIGER*

RELATED CASES

This application is a continuation of application Ser. No. 08/566,487, filed Dec. 4, 1995 now abandoned, which is a continuation of application Ser. No. 08/421,294, filed Apr. 13, 1995, now abandoned which is a continuation of application Ser. No. 08/008,095, filed Jan. 22, 1993, abandoned, which is a continuation of U.S. patent application Ser. No. 07/830,483, filed Feb. 4, 1992, now abandoned which is a continuation of U.S. patent application Ser. No. 07/474,466 filed Feb. 2, 1990, now abandoned.

BACKGROUND OF THE INVENTION

This invention relates to fungi which produce D-glucose oxidase, methods of obtaining such fungi and the use of such fungi to obtain oxidase.

It is known to utilize fungi to produce oxidase. Moreover, it is known to select mutants that produce increased proportions of enzymes from cultures of wild type fungi.

One prior art fungus producing D-glucose oxidase as an adaptive or induced enzyme is the wild type fungus *Aspergillus niger*. This fungus and a method of obtaining D-glucose oxidase are described in U.S. Pat. No. 3,102,081. The prior art wild type *Aspergillus niger* is not as suitable for producing D-glucose as desired under current demand conditions for D-glucose because: (1) it produces substantially larger amounts of gluconate constituitively and a smaller amount of D-glucose oxidase when induced, whereas demand conditions now favor a higher proportion of D-glucose oxidase and the market for D-glucose oxidase is growing faster than for gluconate; and (2) the wild type *Aspergillus niger* requires a large amount such as 0.5M glucose to induce the production of D-glucose oxidase.

It has been proposed to obtain mutants of *Aspergillus niger* that produce a higher yield of D-oxidase. One known method for selecting mutants of a fungus, which mutants have a higher production of the enzyme than a wild-type fungus includes exposing the wild type fungus to a mutagen and screening survivors for increased titers of the enzyme. This method, as practiced in the prior art, has the disadvantage of being long and tedious because of the time and effort required to select the fungi that create the higher titer of the enzyme.

Another prior art process for selecting and growing mutants of fungus is described in U.S. Pat. No. 4,115,197. This patent describes a process in which the mutants are selected through the use of an antibiotic to which the mutants are resistant. This prior art process has the disadvantages of: (1) requiring antibiotics and a further separation step; and (2) generally not selecting for unrelated metabolites.

It is also known to detect mutants by the change in pH caused by action of an enzyme on a substrate. This prior art teaches the use of pH detectors that indicate pH conditions of 5 or 6. These pH detectors are not suitable for detection of enzymes that change acidity in the already acid substrate of *Aspergillus niger*.

SUMMARY OF THE INVENTION

Accordingly, it is an object of the invention to provide novel cultures of fungi capable of producing oxidase.

It is a further object of the invention to provide novel mutants capable of producing oxidase.

It is a still further object of the invention to provide a novel fungus capable of producing D-glucose oxidase constitutively.

It is a further object of the invention to provide a novel method for selecting mutants of fungi that produce oxidase.

It is a still further object of the invention to provide novel cultures of mutants of *Aspergillus niger*.

It is a still further object of the invention to provide a novel technique for selecting mutants of *Aspergillus niger*.

In accordance with the above and further objects of the invention, a mutant of a fungus which produces glucose oxidase is grown and the oxidase is obtained from the culture for commercial use. The oxidase-producing mutants developed by the techniques of this invention are fungi that constitutively produce oxidase but are otherwise of the same known taxonomy and morphology of other fungi that produce the oxidase enzyme as an adaptive or induced enzyme.

In the preferred embodiment, the mutants have the same taxonomy and morphology as wild *Aspergillus niger*, but unlike wild *Aspergillus niger* constitutively synthesize glucose oxidase. They are maintained in a private depository at the University of Nebraska-Lincoln under accession numbers LGF-12, LGF-13, LGF-14, LGF-16, LGF-17, LGF-21, LGF-23 and LGF-25.

To obtain the mutants, fungus that have the desired oxidase induced are grown on a substrate under conditions that permit or encourage mutation, such as by treatment with a mutagen. They are screened for production of increased oxidase and/or production of oxidase when in the presence of: (1) only low concentration of glucose; or (2) no glucose but instead of glucose another substance that is acted upon by oxidase to create an indication of oxidase. In the preferred embodiment, the fungi are grown in a concentration of glucose that is too low to induce production of oxidase by wild type *Aspergillus niger* and a pH indicator. The mutations are created with the aid of a mutagen prior to screening.

When the indicator shows substantial production of the desired enzyme from fungi grown in low concentration of glucose or no glucose, that culture is removed and multiplied under the assumption that it is a culture of a mutant that constitutively produces the desired enzyme. The fungi that create oxidase constitutively rather than by induction are increased in a medium that includes: (1) an auxiliary carbon source for the fungus to use as a nutrient; and (2) any other substance necessary for the growth of the desired mutants. The fungi may then be used to produce the desired oxidase.

In one embodiment, mutants of wild type *Aspergillus niger* are obtained by inoculating spores of wild type *Aspergillus niger* onto a media containing: (1) some D-glucose as a nutrient but in a concentration insufficient to induce *Aspergillus niger* to produce D-glucose oxidase; (2) an auxiliary carbon source; and (3) methyl red or other compound that indicates acidity. For some subspecies of *Aspergillus niger* the concentration of glucose that is insufficient for induction of oxidase is 0.1 molar glucose at 30 degrees centigrade. The concentration should be lower than 0.2M and the temperature lower than 40 degrees centigrade.

The cultures are incubated and then surveyed for colonies with a red ring around them surrounded by other smaller colonies without the red ring. The colonies with the red ring around them are mutants which constitutively synthesize D-glucose oxidase in sufficient quantities to produce enough D-gluconic acid to acidify the media. The mutants obtained from this technique are grown, usually under different optimum temperature and nutrient conditions, and the enzyme harvested.

This process has several advantages, such as: (1) it provides a high proportion of oxidase and a lower amount of less valuable by-products; and (2) it enables the selection of mutants which are capable of producing substantial quantities of oxidase.

DETAILED DESCRIPTION

The oxidase-producing fungi developed by the techniques of this invention are fungi that constitutively produce D-glucose oxidase (FAD: oxide reductase; or aerodehydrogenase) but are otherwise of the same known taxonomy and morphology of other fungi which produce oxidase as a adaptive or induced enzyme. In the preferred embodiment, the fungi are of the same genus and species as wild *Aspergillus niger*, but unlike wild *Aspergillus niger* the mutant fungi constitutively synthesize glucose oxidase. They produce glucose oxidase when grown in a medium having less than 0.2M (molar) glucose at a temperature lower than 40 degrees Centigrade. They are maintained in a private depository at the University of Nebraska-Lincoln under accession numbers LGF-12, LGF-13, LGF-14, LGF-21, LGF-23 and LGF-25 stored as a lyophylized spores in a freezer in Room 107 Biochemistry Hall, East Campus, University of Nebraska-Lincoln. Samples of cultures may be obtained by contacting Dr. John Markwell, Department of Biochemistry, University of Nebraska, Lincoln, Nebr. 68583-0718, phone: 472-2924.

To obtain fungi which produce oxidase constitutively, fungi which produce the oxidase when induced are cultured in a substrate having a pH-sensitive indicator. The substrate for the fungi is at a concentration too low to induce the production of significant acidity by reduction of an ingredient of the substrate by the known genus and species from which mutants are to be selected. The pH indicator does not indicate acid visually in the normal substrate of the culture unless the mutant is producing the enzyme in quantities large enough to indicate that the mutant is producing the enzyme constitutively.

If the parental fungus is *Aspergillus niger*, the indicator must at least distinguish pH values between 8 and 3 from those above 8 and those below 3 but preferably distinguish pH values between 6 and 3 from those above 6 and those below 3. Some other indicators are suitable under some circumstances to indicate the acidifiction of the medium by microbes and these are: phenol red, bromothymol blue, neutral red, bromcresol purple, chlorophenol red, methyl red, bromocresol green, bromophenol blue, and methyl yellow. However, the indicator should be selected in accordance with the acidification level indicating oxidase activity in the medium. Other microorganisms are known that produce glucose oxidase and this method of obtaining mutants that produce a large portion of glucose oxidase is applicable to them. Some other microorganisms are *Penicillium notatum, Polyporus obtusus* and *Phanerochaete chrysosporium*.

In one embodiment, glucose oxidase producing fungi are selected from the genus and species *Aspergillus niger* by culturing these fungi on an auxiliary carbon source, a pH-sensitive indicator and D-glucose at a low concentration below that which triggers the production of D-glucose oxidase in the fungus. When the culture shows portions that are more acidic and larger than background portions, these portions are removed and separately increased.

More specifically, the *Aspergillus niger* are suspended in a sterilized medium. Later, they are inserted on the surface of plates containing layers of glycerol, D-glucose and methyl red. It may also include Agar or other filler material. The D-glucose is at a low concentration and in the case of *Aspergillus niger*, 0.1M or less.

The plates are incubated in the dark at 25 degrees Centigrade for five days and then examined. Large colonies surrounded by a red-colored zone on a background of small colonies are selected, removed and increased. These colonies yield mutants that constitutively produce glucose oxidase.

In use, the mutants are grown in a culture having D-glucose at a lower concentration than 0.5M and at a concentration closer to 0.1M for at least four days at a temperature between 25 and 40 degrees Centigrade. The glucose oxidase is harvested in a conventional manner such as by filtering off and lysis of the mycelium cells. A suitable technique for harvesting the enzyme is described in U.S. Pat. No. 3,102,081 to Faucett et al. granted Aug. 27, 1963. Other sources of information on production of glucose oxidase is described in "The Filamentation Fungi", volume 1, *Industrial Mycolog*, Edited by John E. Smith and David R. Berry, published by Edward Arnold Publishers, Limited, 25 Hill Street, London W1X8LL, the disclosure of which is incorporated by reference herein. More specifically, such information is produced in Chapter 8 of this book entitled "Organic Acid Production" by L. B. Lockwood.

The invention is illustrated by the following examples:

EXAMPLES

MATERIALS AND METHODS
1. Organism and Media.

Wild type *Aspergillus niger* NRRL-3 (ATCC No. 9029), was grown on plates of enriched medium consisting of 20 g (grams) malt extract, 20 g glucose, 1.0 g peptone and 20 g agar (Difco) in 1.0 L water or on a solid carbohydrate-mineral salts medium (3.0 g $NaNO_3$, 1.0 g $K_2HPO_4$, 0.5 g $MgSO_4.7H_2O$, 0.5 g KCl, 0.01 g $FeSO_4.7H_2O$, 20.0 g glycerol, 18 g glucose and 15 g agar in a liter of medium). Sugars were autoclaved separately. Liquid carbohydrate-mineral salts medium was similar to the solid medium, except that agar was omitted.

2. Mutagenesis and Selection.

Suspensions of *Aspergillus niger* spores were prepared from enriched medium petri plates of the organism using sterile water containing 0.025% (vol/vol) Triton X-100. The $A_{650}$ of the suspension was measured after filtering through sterile Miracloth (Calbiochem).

The spore suspension was diluted to produce a final absorbance of 0.15 in a 1 cm (centimeter) cuvette. This concentration is equivalent to $7.5 \times 10^5$ colony forming units per milliliter. A two-milliliter volume of the suspension was incubated at room temperature on a shaker at 200 rpm for three hours to permit hydration. The spores were harvested by centrifugation, were resuspended in 1.8 mL of 0.1M sodium acetate buffer (pH 4.4) and treated with 200 L of sodium nitrite (5 mg $mL^{-1}$) solution which generated the mutagenic agent, nitrous acid, in the sodium acetate buffer.

The suspension was shaken at room temperature for 2 hours, the spores were concentrated by centrifugation, rinsed with two 10 mL portions of 50 mM phosphate buffer (pH 7.0), and finally resuspended in 2 mL of liquid carbohydrate-mineral salts medium. Aliquots of 50 L of spores exposed to mutagen were plated on diagnostic agar consisting of the solid carbohydrate-mineral salts media also containing 0.001 percent (wt/vol) methyl red (Sigma).

After five days incubation at 25 degrees Centigrade, the diagnostic plates were examined for colonies surrounded by pink zones in the medium. These selected colonies were streaked for purification on identical diagnostic medium. Control spore suspensions were treated identically except that sodium nitrite exposure was omitted. The above mutagenesis conditions resulted in a mutation frequency for the above phenotype of approximately $6.6 \times 10^{-6}$.

After mutagenesis of conidia with nitrous acid, the conidia were plated on diagnostic mineral medium containing 2 percent (wt/vol) glycerol, 0.1M D-glucose and methyl red. After five days of growth, the plates had a background of pinpoint-sized white colonies. Presumed mutants appeared as white or yellowish colonies approximately 0.5 to 1 cm in diameter, surrounded by reddish circular zones. The red zones were attributed to the production of acid by the colony. Such presumed mutants exhibited black conidia on aerial conidiophores, characteristic of the parental *Aspergillus niger*. Single spore isolates of presumed mutants with this phenotype were obtained by repeated streaking on diagnostic mineral medium and selection of isolated colonies. Such isolated strains were maintained on slants or plates of enriched medium.

3. Growth in Liquid Medium and Preparation of Extracts.

Spores from purified strains were inoculated into 60 mL (milliliter) of liquid carbohydrate-mineral salts medium in a 125 mL flask and grown for five days at 25 degrees Centigrade on a rotary shaker set at 200 revolutions per minute. Cultures were filtered through Miracloth and washed with distilled water. The mycelia were ground in a mortar and pestled with about 0.2 g sand and 20 mL 0.1M sodium acetate buffer pH 5.2. The entire mixture was filtered (Whatman No. 1). The clear filtrate was retained for analysis.

4. Assays.

Samples were assayed for protein using the BCA protein reagent (Smith et al. 1985) (Pierce Chemical Company). Assays for glucose oxidase (Ciucu and Patroeseu 1984) were performed at 25 degrees Centigrade in cuvettes with a 1.0 cm path length using 1.4-benzoquinone (Sigma) as an electron acceptor.

5. Assay for D-Gluconate Production.

Extracts of the NRRL-3 and mutant strains, grown on the liquid mineral salts medium containing 2 percent (wt/vol) glycerol and 0.1M D-glucose, were desalted by chromatography on columns of Sephadex G-25 equilibrated with 0.1M sodium acetate buffer (pH 5.2). An aliquot of each extract containing 5 mg of protein was incubated in a 10 mL volume containing 0.5 millimoles sodium citrate (pH 5.0), 0.05 millimoles of D-glucose and 100 units of bovine liver catalase (EC 1.11.1.6) (Calbiochem).

The solution in a 50 mL flask was shaken at 200 rpm in a 25 degrees Centigrade incubator for 1 hour and a 2 mL aliquot removed and filtered through a Centricon 10 centrifugal concentrator (Amicon Corp.). Aliquots of the filtrate were assayed for D-gluconate by an end-point assay in 1 mL total volume containing 0.1 millimoles Tris Cl (pH 8.6), 1 mol ATP, 10 mol $MgCl_2$, 1 mol NADP+, and sufficient amounts of *Escherichia coli* gluconate kinase (EC 2.7.1.12) (Sigma) and yeast 6-phosphogluconate dehydrogenase (EC 1.1.1.44) (Sigma) to produce a final, stable $A_{340}$ within 10 minutes at 30 degrees Centigrade. This experiment was performed on three separate occasions and the results reported are the mean of these determinations.

SPECIFIC EXAMPLES

*Aspergillus niger* was obtained from NRRL 3. It was grown as follows:

The following components were mixed to obtain one liter of final volume—1.5 g (grams) of sodium nitrate ($NaNO_3$); 0.5 g potassium ($K_2HPO_4$); 0.25 g hydrated magnesium sulfate ($MgSO_4(7H_2O)$); 0.25 g potassium chloride (KCl); 0.005 g ferra sulfate ($FeSOP_4(7H_2O)$); 20 g glycerol; 18 g D-glucose; 15 g Agar; 0.01 g methyl red.

This mixture was autoclaved and cooled to 50 degrees Centigrade. Thirty milliliters of it is poured into 100×15 mm Petri plates and allowed to solidify. Conidia of *Aspergillus niger* are suspended in the medium as described above except for glycerol, D-glucose, Agar and Methyl red in a small volume which are spread over the surface of the plates with a sterile, bent glass rod. The glycerol and D-glucose, Agar and methyl red are separately autoclaved and mixed in the proper proportions with the solidified mixture.

The plates were then incubated in the dark at 25 degrees Centigrade for five days and examined for the presence of large colonies surrounded by a red colored zone on a background of small colonies which have not changed yellowish color of the medium. A final concentration of 0.001 percent weight/volume methyl red produces readily observed colored changes of red on a yellow background. The culture of the red on the yellow background was selected for increasing.

Twenty-six such presumptive mutants were grown at 25 degrees Centigrade in liquid mineral salts medium containing 2 percent (wt/vol) glycerol and 0/01, 0.1 or 0.5M D-glucose. After five days of growth, the mycelia were harvested and homogenized. The glucose oxidase activity of the extract was measured using a spectrophotometric assay measuring the reduction of 1.4-benzoquinone. Seven of these strains showed a marked increase in glucose oxidase specific activity relative to the parental strain as shown in Table I. The table shows glucose oxidase specific activity (micromoles benzoquinone reduced per minute per milligram of protein of parental and mutuant strains of *Aspergillus niger*. The number in

TABLE I

| Strain | D-Glucose Concentration in Growth Medium | | |
|---|---|---|---|
| | 0.01 M | 0.1 M | 0.5 M |
| NRRL-3 | 0.059 (0.011) [4] | 0.040 (0.014 [8] | 0.075 (0.022) [7] |
| LGF-13 | 0.17 (0.020) | 0.12 (0.009) | 0.68 (0.24) |
| LGF-14 | 0.34 (0.068) | 0.80 (0.20) | 0.85 (0.26) |
| LGF-16 | 0.12 (0.031) | 0.172 (0.984) | 0.11 (0.015) |
| LGF-17 | 0.13 (0.022) | 0.28 (0.050) | 0.14 (0.030) |
| LGF-21 | 0.19 (0.064) | 0.15 (0.041) [4] | 0.16 (0.064) |
| LGF-23 | 0.042 (0.004) | 0.85 (0.22) [4] | 0.77 (0.098) |
| LGF-25 | 0.039 (0.006) | 0.10 (0.018) | 0.29 (0.098) | parentheses indicates the standard error of the mean for separate cultures grown at 25 degrees Centigrade for 5 days. Unless a number in brackets is present to indicate the number of separate samples assayed, the value represents the average of three cultures.

To corroborate that the activity measured in the above assay was indeed glucose oxidase, extracts of the NRRL-3, LGF-14 and LGF-23 strains were incubated with D-glucose for one hour and aliquots of the incubation enzymatically assayed for D-gluconate production. Using an extract of the NRRL-3 parental strain, the conversion of D-glucose to D-gluconate occurred with 92 percent of the expected yield. The conversion of D-glucose to D-gluconate using extracts of the LGF-14 and LGF-23 strains was 88 percent and 94 percent, respectively.

The mutants of *Aspergillus niger* NRRL-3 of this invention increased glucose oxidase specific activity over the NRRL-3 strain of *Aspergillus niger* which itself is a strong producer of glucose oxidase and has been used in commercial fermentative production of D-gluconate.

The mutant strains isolated using this selection system were grown at D-glucose concentrations (0.01 and 0.1M)

below those normally used for industrial fermentations, as well as at 0.5M which approximates the initial concentration for commercial production of D-gluconate. The mutant strains covered herein (LGF-12, LGF-13, LGF-14, LGF-16, LGF-17, LGF-21, LGF-23 and LGF-25) demonstrated a marked increase in glucose oxidase specific activity for at least two of the glucose concentrations. Several of the mutant strains clearly contain higher specific activity of glucose oxidase in cultures grown on all three concentrations of D-glucose (e.g., LGF-12 and LGF-14).

The selection scheme for mutants proved effective at production of mutants of *Aspergillus niger* with higher than usual specific activities of glucose oxidase activity. The biosynthesis of glucose oxidase involves multiple processing steps, e.g. phosphorylation and sequential glycosidation events and coordinate synthesis of the flavin adenine dinucleotide cofactor, so it would be simplistic to expect that a single gene alteration would be sufficient to optimize production of the enzyme. However, marked increases in specific activity are possible with direct mutagenesis and detection techniques.

The above fungi and procedure for obtaining and using them have the advantages of: (1) producing large amounts of oxidase without as much nutrient or effort as required when primary metabolites not in demand are produced; (2) enabling the selection of metabolites that are more efficient in producing oxidase; and (3) permitting the efficient production of oxidase.

Although a specific embodiment of the invention has been described with some particularity, many modifications and variations in the embodiment are possible without deviating from the invention. Accordingly, it is to be understood that, within the scope of the appended claims, the invention may be practiced other than as specifically described.

What is claimed is:

1. A biologically pure culture of *Aspergillus niger* which constitutively synthesizes glucose oxidase when grown in a medium having less than 0.1M glucose and having the accession number NRRL 18927.

* * * * *